US007785301B2

(12) United States Patent
Yuzhakov

(10) Patent No.: US 7,785,301 B2
(45) Date of Patent: Aug. 31, 2010

(54) TISSUE CONFORMING MICRONEEDLE ARRAY AND PATCH FOR TRANSDERMAL DRUG DELIVERY OR BIOLOGICAL FLUID COLLECTION

(76) Inventor: Vadim V Yuzhakov, 17555 Atlantic Blvd., Suite 1404, Sunny Isle Beach, FL (US) 33160-2995

( * ) Notice: Subject to any disclaimer, the term of this patent is extended or adjusted under 35 U.S.C. 154(b) by 0 days.

(21) Appl. No.: 11/563,892

(22) Filed: Nov. 28, 2006

(65) Prior Publication Data
US 2008/0125743 A1    May 29, 2008

(51) Int. Cl.
*A61M 5/32* (2006.01)
(52) U.S. Cl. .................. 604/272; 604/46; 604/180
(58) Field of Classification Search ............ 604/46, 604/173, 180, 272, 506, 273, 274
See application file for complete search history.

(56) References Cited

U.S. PATENT DOCUMENTS

| | | | |
|---|---|---|---|
| 2,893,392 A | 7/1959 | Wagner et al. | |
| 3,072,122 A | 1/1963 | Rosenthal | |
| 3,814,097 A | 6/1974 | Ganderton et al. | |
| 3,964,482 A | 6/1976 | Gerstel et al. | |
| 4,983,377 A | 1/1991 | Murphy et al. | |
| 4,983,418 A | 1/1991 | Murphy et al. | |
| 5,547,467 A | 8/1996 | Pliquett et al. | |
| 5,667,491 A | 9/1997 | Pliquett et al. | |
| 5,911,223 A | 6/1999 | Weaver et al. | |
| 6,083,196 A * | 7/2000 | Trautman et al. | 604/46 |
| 6,256,533 B1 | 7/2001 | Yuzhakov et al. | |
| 6,312,612 B1 | 11/2001 | Sherman et al. | |
| 6,334,856 B1 | 1/2002 | Allen et al. | |
| 6,379,324 B1 | 4/2002 | Gartstein et al. | |
| 6,451,240 B1 | 9/2002 | Sherman et al. | |
| 6,471,903 B2 | 10/2002 | Sherman et al. | |
| 6,503,231 B1 | 1/2003 | Prausnitz et al. | |
| 6,537,264 B1 * | 3/2003 | Cormier et al. | 604/506 |
| 6,565,532 B1 | 5/2003 | Yuzhakov et al. | |
| 6,611,707 B1 | 8/2003 | Prausnitz et al. | |
| 6,652,478 B1 | 11/2003 | Gartstein et al. | |
| 6,743,211 B1 | 6/2004 | Prausnitz et al. | |
| 6,931,277 B1 | 8/2005 | Yuzhakov et al. | |
| 2002/0020688 A1 | 2/2002 | Sherman et al. | |
| 2002/0082527 A1 | 6/2002 | Liu et al. | |
| 2002/0082543 A1 | 6/2002 | Park et al. | |
| 2002/0138049 A1 | 9/2002 | Allen et al. | |
| 2002/0168290 A1 | 11/2002 | Yuzhakov et al. | |

(Continued)

*Primary Examiner*—Kevin C Sirmons
*Assistant Examiner*—Bhisma Mehta
(74) *Attorney, Agent, or Firm*—Sutherland Asbill & Brennan LLP

(57) ABSTRACT

Microneedle arrays are provided for use on a contoured or flexible tissue surface. In one embodiment, the microneedle array includes a plurality of microneedles, each having a base portion, a tip end portion distal to the base portion, and body portion therebetween; and a flexible substrate which comprises a plurality of apertures, each of which are defined by (i) a plurality of substrate elements which are integral with the base portions of the microneedles, and (ii) at least one spring element connecting at least two of the substrate elements. The spring element may include a curved element, such as a C-shaped, U-shaped, or S-shaped element. Apertures may be defined, for example, by two substrate elements, which connected to three or four spring elements. A skin patch is provided for therapeutic or diagnostic applications, which includes the microneedle array and an adhesive material.

24 Claims, 8 Drawing Sheets

U.S. PATENT DOCUMENTS

| | | |
|---|---|---|
| 2002/0177858 A1 | 11/2002 | Sherman et al. |
| 2003/0028087 A1 | 2/2003 | Yuzhakov et al. |
| 2003/0028125 A1 | 2/2003 | Yuzhakov et al. |
| 2003/0143113 A2 | 7/2003 | Yuzhakov et al. |
| 2003/0150745 A1 | 8/2003 | Teodorczyk et al. |
| 2003/0199810 A1* | 10/2003 | Trautman et al. ............ 604/46 |
| 2003/0208167 A1 | 11/2003 | Prausnitz et al. |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212346 A1 | 11/2003 | Yuzhakov et al. |
| 2003/0223906 A1 | 12/2003 | McAllister et al. |
| 2004/0106904 A1 | 6/2004 | Gonnelli et al. |
| 2005/0049549 A1 | 3/2005 | Wong et al. |
| 2005/0137525 A1 | 6/2005 | Wang et al. |
| 2005/0137531 A1 | 6/2005 | Prausnitz et al. |
| 2005/0187525 A1 | 8/2005 | Hilgers et al. |
| 2005/0209565 A1 | 9/2005 | Yuzhakov et al. |
| 2005/0261631 A1* | 11/2005 | Clarke et al. ................ 604/173 |

* cited by examiner though a polymeric or metal microneedle base can be slightly bent in one direction, such arrays of microneedles cannot readily be applied to convex or concave skin surfaces or stretched in different directions. Thus, a patch having such a microneedle array may tend to fall off the skin surface as the patient moves, particularly for patches designed to be continuously worn even on relatively flat areas of a patient's skin, due to the significant stretching of the skin that occurs during normal movement. It therefore would be desirable to provide a microneedle array that can improve penetration control into contoured skin surfaces and lessen premature movement of microneedles out of optimum penetrated position. It also would be desirable to provide a better microneedles array, and patch, for transdermal drug delivery or transdermal biological sample collection over an extended period.

TISSUE CONFORMING MICRONEEDLE ARRAY AND PATCH FOR TRANSDERMAL DRUG DELIVERY OR BIOLOGICAL FLUID COLLECTION

BACKGROUND OF THE INVENTION

This invention is generally in the field of devices for the administration of drugs to patients and devices for biological sample collection through the skin. More particularly this invention relates to microneedle array devices and methods for transdermal drug delivery, for transdermal diagnostic sampling of biological fluids, or for a combination thereof.

Microneedles and microneedle arrays have been disclosed for use in the fields of transdermal drug delivery and biological sample collection. Transdermal drug delivery provides several advantages over other routes for administering a drug formulation to a patient. For example, oral administration of some drugs may be ineffective because the drug is destroyed in the gastrointestinal tract or eliminated by the liver, both of which are avoided by transdermal drug delivery. Parenteral injection with a conventional hypodermic needle also has its drawbacks, as it is painful and inconvenient. It would, however, be advantageous to provide improved microneedle devices and methods for transdermal drug delivery. Analyte concentration determination in biological samples withdrawn transdermally is important for a variety of diagnostic applications. For example, collection of blood or interstitial fluids is often necessary, for example, to measure glucose for diabetes management, or to measure cholesterol for monitoring cardiovascular conditions. Conventional devices and methods may involve cumbersome and complicated devices and procedures, or may be painful. It would be advantageous to provide devices and diagnostic methods that are relatively simple to use and pain free, in order to improve patient compliance with diagnostic monitoring and disease management.

In both transdermal drug delivery and transdermal biological sampling using microneedle arrays, particularly in patch-type devices, it would be particularly desirable for the microneedles to remain in their precise, penetrated position through the stratum corneum to maintain the fluid communication between a drug or sample collection reservoir and the tissues beneath the stratum corneum for an extended period. However, the skin of a patient is contoured and quite flexible. Thus, it may be difficult for a conventional microneedle array having a rigid, planar substrate to maintain the desired microneedle penetration, particularly where the microneedle array is part of a patch device and the patient (and consequently, his or her skin) ordinarily moves about and flexes throughout the extended period of microneedle array (e.g., patch) application. For example, a microneedle array having base made of silicon is flat and inflexible, and even though a polymeric or metal microneedle base can be slightly bent in one direction, such arrays of microneedles cannot readily be applied to convex or concave skin surfaces or stretched in different directions.

SUMMARY OF THE INVENTION

In one aspect, microneedle arrays are provided for use on a contoured or flexible tissue surface. In one embodiment, the microneedle array includes a plurality of microneedles, each having a base portion, a tip end portion distal to the base portion, and body portion therebetween; and a flexible substrate which comprises a plurality of apertures, each of which are defined by (i) a plurality of substrate elements which are integral with the base portions of the microneedles, and (ii) at least one spring element connecting at least two of the substrate elements. The spring element may include a curved element, such as a C-shaped, U-shaped, or S-shaped element. In one embodiment, at least one of the apertures is defined by two substrate elements. In one embodiment, each substrate element is connected to three or four spring elements.

In one embodiment of the microneedle array, at least one of the plurality of microneedles has a channel extending substantially from the base portion through at least a part of the body portion, the channel being open along at least part of the body portion and in fluid communication with at least one of the apertures in the substrate. The base portion of the at least one of the microneedles may be untapered and have a substantially rectangular cross-sectional shape in a plane parallel to the substrate. The at least one channel may be open to two opposing surfaces of the microneedle. The tip end portion of the at least one of the microneedles may be tapered, and, in one embodiment, the at least one channel extends into the tapered tip portion.

In one embodiment, the flexible substrate and the microneedles may be formed of a biocompatible metal, such as a stainless steel, or formed of a polymer. In one embodiment, the length of the plurality of microneedles may be between 100 µm and 500 µm.

In one aspect, a device is provided for transdermal administration of a drug. In one embodiment, the device includes a microneedle array that has a plurality of microneedles, each having a base portion, a tip end portion distal to the base portion, and body portion therebetween; a flexible substrate which comprises a plurality of apertures, each of which are defined by (i) a plurality of substrate elements which are integral with the base portions of the microneedles, and (ii) at least one spring element connecting at least two of the substrate elements; and at least one drug storage element, which contains a drug formulation, disposed adjacent to the microneedle array. The drug delivery device may further include a release mechanism for releasing the drug formulation from the drug storage element to permit the drug formulation to pass through the apertures of the substrate of the microneedle array. The drug storage element may be attached to a first surface of the substrate, the first surface being opposed to a second surface of the substrate of the microneedle array, wherein the microneedles project from said second surface. The drug storage element may be in the form of a coating on the surfaces of the microneedles, on the substrate, or on both the microneedles and substrate. The drug storage element, in one embodiment, can flex and deform with substrate of the microneedle array. In one embodiment, the drug storage element comprises a porous material, wherein the drug formulation is stored in pores of the porous material. The device may further include an adhesive surface suitable for securing the device to the skin of a patient during administration of the drug formulation to the patient, and/or a removable release liner, which covers the microneedles and apertures prior to use of the device.

In another aspect, a device is provided for transdermal sampling of a biological fluid. In one embodiment, the device includes a microneedle array that has a plurality of microneedles, each having a base portion, a tip end portion distal to the base portion, and body portion therebetween; a flexible substrate which comprises a plurality of apertures, each of which are defined by (i) a plurality of substrate elements which are integral with the base portions of the microneedles, and (ii) at least one spring element connecting at least two of the substrate elements; and at least one collection reservoir for retaining a biological fluid sample drawn through the microneedle array adjacent thereto. The device may further include a sensor for testing a biological fluid retained in the collection reservoir.

In yet another aspect, a method is provided for manufacturing a microneedle array. The method includes (a) forming a flexible substrate which comprises a plurality of apertures, each of which are defined by (i) a plurality of substrate elements, and (ii) at least one spring element connecting at least two of the substrate elements; and (b) forming a plurality of microneedles, each having a base portion, a tip end portion distal to the base portion, and body portion therebetween, wherein the base portions of the microneedles are integral with the substrate elements. In one embodiment, the method includes forming in a planar substrate material the plurality of apertures, the plurality of substrate elements, and the plurality of spring elements, by removing selected portions of the substrate material. The removal process may include embossing, injection molding, casting, photochemical etching, electrochemical machining, electrical discharge machining, precision stamping, high-speed computer numerically controlled milling, Swiss screw machining, soft lithography, directional chemically assisted ion etching, laser cutting, or a combination thereof.

In one particular embodiment, a skin patch is provided for therapeutic or diagnostic applications. In one case, the patch includes (a) a microneedle array which comprises a plurality of microneedles, each having (i) a base portion, a tip end portion distal to the base portion, and body portion therebetween, and (ii) a channel extending substantially from the base portion through at least a part of the body portion, the channel being open along at least part of the body portion; (b) a flexible substrate which comprises a plurality of apertures, each of the apertures being defined by (i) two or more substrate elements which are integral with the base portions of the microneedles, and (ii) at least two spring elements connected to the two or more substrate elements, wherein the channels of the microneedles are in fluid communication with at least one of the apertures in the substrate; and (c) an adhesive material for securing the microneedle array to a patient's skin with the microneedles inserted into the stratum corneum.

In another aspect, a method is provided for administering a drug to a patient in need thereof. The method may include inserting into the skin of the patient the microneedles of the microneedle array described herein, to form holes in the stratum corneum; and then causing a fluid drug formulation to be transported through the apertures of the substrate of the microneedle array and then through the holes in the stratum corneum, while the microneedles remain positioned in the holes. In still another aspect, a method is provided for transdermally collecting a biological fluid sample from a patient. The method may include inserting into the skin of the patient the microneedles of the microneedle array described herein, to form holes in the stratum corneum; and causing the biological fluid to be withdrawn from the patient through the holes in the stratum corneum and then through the apertures of the substrate of the microneedle array, while the microneedles remain positioned in the holes. In either of these methods, the area of the skin where the microneedles are inserted may be in a body area that is routinely moved or highly flexed, such as the back, neck, knee, etc.

DETAILED DESCRIPTION OF THE PREFERRED EMBODIMENT

Figure 1:
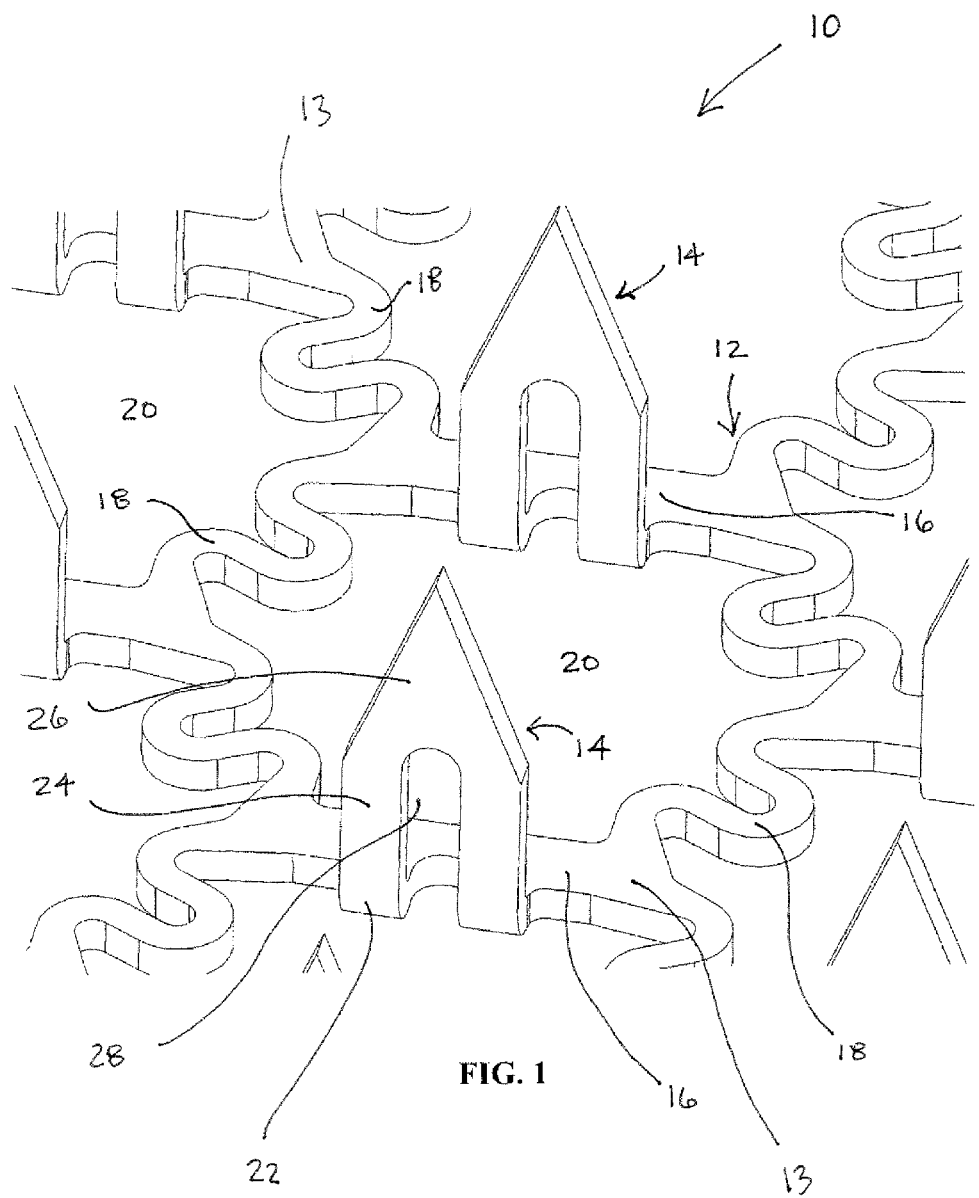
FIG. 1 is a close-up, perspective view of part of one embodiment of a microneedle array as described herein.

Microneedle arrays have been developed which can be elastically stretched and deformed to better conform with contoured and flexible tissue surface. The substrate of the array is flexible and elastically deformable (i.e., stretchable). Continuous wear devices (e.g., a skin patch) incorporating these microneedle arrays advantageously can be stretched or compressed in essentially any direction as a patient's skin stretches and changes contours during normal movement, beneficially maintaining the microneedles in their inserted position during extended transdermal drug delivery or diagnostic applications. That is, in one embodiment, the microneedle array comprises one or more swing elements configured to allow the substrate to stretch when the microneedle array is attached to and worn on the tissue surface.

The flexibility of the microneedle array is provided by a substrate design having a network of interconnected spring elements. In one embodiment, apertures in the substrate are defined by (i) a plurality of substrate elements which are integral with the base portions of the microneedles, and (ii) at least one spring element connecting at least two of the substrate elements. Each spring element essentially functions as a microspring or hinge. The spring element is capable of absorbing and storing mechanical energy when stretched, compressed, bent, and/or twisted by an external load so that the spring element will regain its original shape once the load is removed. The array of spring elements impart flexibility to at least a portion of the substrate so as to allow the microneedle array to conform to contours of the skin surface structure.

In a preferred embodiment, the microneedle array advantageously includes microneedles having a strong, small solid tip capable of piercing the stratum corneum into the patient's lower skin tissues (e.g., epidermis, dermis, or subcutaneous skin layers), while the flexible substrate enables the microneedles to both conform to the contoured skin surface during initial penetration of the microneedles and to remain in this inserted position as the contoured skin surface changes during natural movements of the patient. Moreover, the ability of the microneedle array to flexibly or elastically deform reduces the likelihood that the array is bent or broken while being worn by the patient because it is capable of yielding to forces that would otherwise break a rigid microneedle array. Thus, any dangers that may be posed by a broken microneedle array are lessened or avoided. A still further advantage of the present microneedle array is that it may be fabricated using relatively easy and relatively inexpensive techniques, since the flexible structures can be formed from the substrate material.

As used herein, the terms "comprise," "comprising," include," and "including" are intended to be open, non-limiting terms, unless the contrary is expressly indicated.

Microneedle Array

In one embodiment, the microneedle array includes a plurality of microneedles, each having a base portion, a tip end portion distal to the base portion, and body portion therebetween; and a flexible substrate which comprises a plurality of apertures, each of which are defined by (i) a plurality of substrate elements which are integral with the base portions of the microneedles, and (ii) at least one spring element connecting at least two of the substrate elements. In various embodiments, the spring element may include a curved element, such as a C-shaped, U-shaped, or S-shaped element, or a combination thereof. Each of the apertures may be defined by one, two, or more substrate elements, and by two, three, four, or more spring elements.

The material of construction and dimensions of the spring element can be tailored to control where/how the spring element flexes. The number, arrangement, and orientation of the spring elements with the substrate elements can be used to control how the whole substrate flexes. A substantially planar substrate formed of a rigid material can be made substantially flexible and/or stretchable by creating arrays of the spring elements, e.g., a network of flexible structures, in the substrate. The shape and thickness of these spring elements can be tailored each material of construction and each array device. The interconnected network of spring elements desirably extends over a substantial area of the substrate, in order to maximize the area of flexibility in the whole substrate, enhancing the ability of the array to conform to and stretch with a variety of contoured tissue surfaces.

It is also envisioned that apertures may be defined by substrate elements (which have microneedles extending therefrom), spring elements, and tertiary elements that neither are spring elements nor have a microneedle extending therefrom. The substrate also may include areas with no apertures, areas with apertures but no spring elements or substrate elements, or both of these types of areas as long as there is sufficient flexibility/stretchability imparted to the whole substrate by the remaining area having spring element-defined apertures.

Each microneedle projects at an angle from the substrate element. Typically, the microneedle is perpendicular to the substrate element. The base portion of the microneedle may include a curved portion transitioning the change in orientation of the microneedle from the substrate element. One, two, or more microneedles may extend from a single substrate element. The substrate element may also include one or more springs or otherwise is designed to flex.

Representative, non-limiting embodiments of the microneedle array are illustrated in FIG. 1 and 2. FIG. 1 shows a microneedle array 10 includes a substantially planar substrate 12 and a plurality of microneedles 14 extending from the substrate 12. The substrate 12 includes substrate elements 16 and spring elements 18, which define apertures 20. The surface 13 of substrate 12 optionally may be coated with an adhesive material (not shown) to enhance securement of the inserted microneedle array to the outer skin or other tissue surface. The base portion 22 of the microneedle 14 integrally connected to the substrate element 16. The microneedle also includes a tip end portion 26 distal to the base portion 22, and a body portion 24 therebetween. The body portion 24 of the microneedle 14 has a substantially rectangular cross-sectional shape in a plane parallel to the substrate 12. The microneedle 14 also has an elongated channel 28 extending from the base portion 22 through the body portion 24, and optionally into the tip end portion 22. The channel 28 is open through two opposing surfaces of the body portion, and the channel 28 is in fluid communication with aperture 20 in the substrate 12. The tip end portion 26 and body portion 24 of the microneedle 14 are substantially perpendicular to the substrate 12, and the base portion 22 of the microneedle 14 includes a curved portion that is integral with the substrate element 16. It is understood, however, that in other embodiments, the microneedle may be of essentially any other design (e.g., in a different shape, with or without channels or bores, etc.).

Figure 2A:
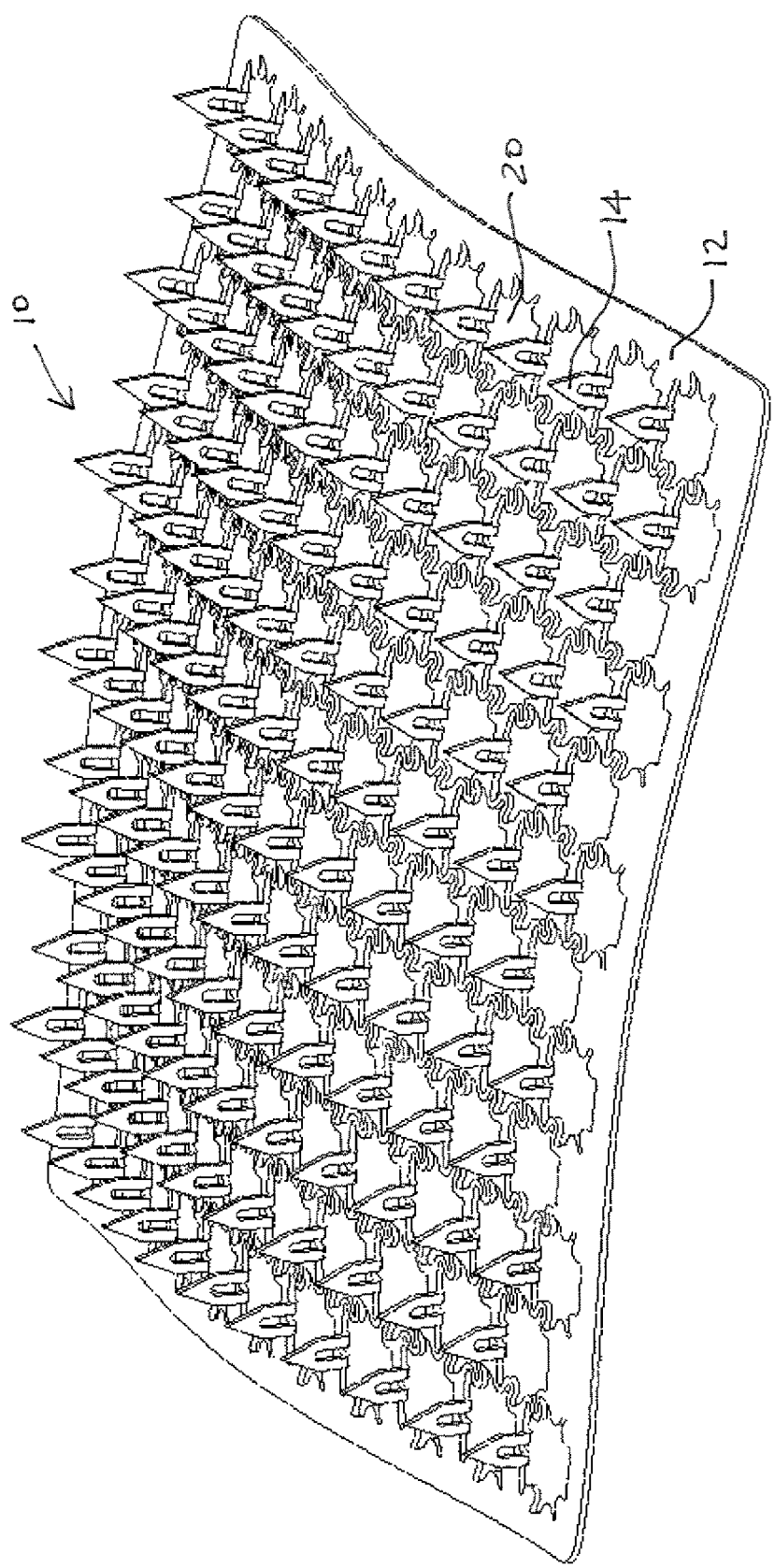
FIG. 2A-D are perspective views of one embodiment of a microneedle array as described herein, illustrating how the array can be elastically deformed to conform to contoured surfaces or elastically stretched in different directions.
Figure 2B:
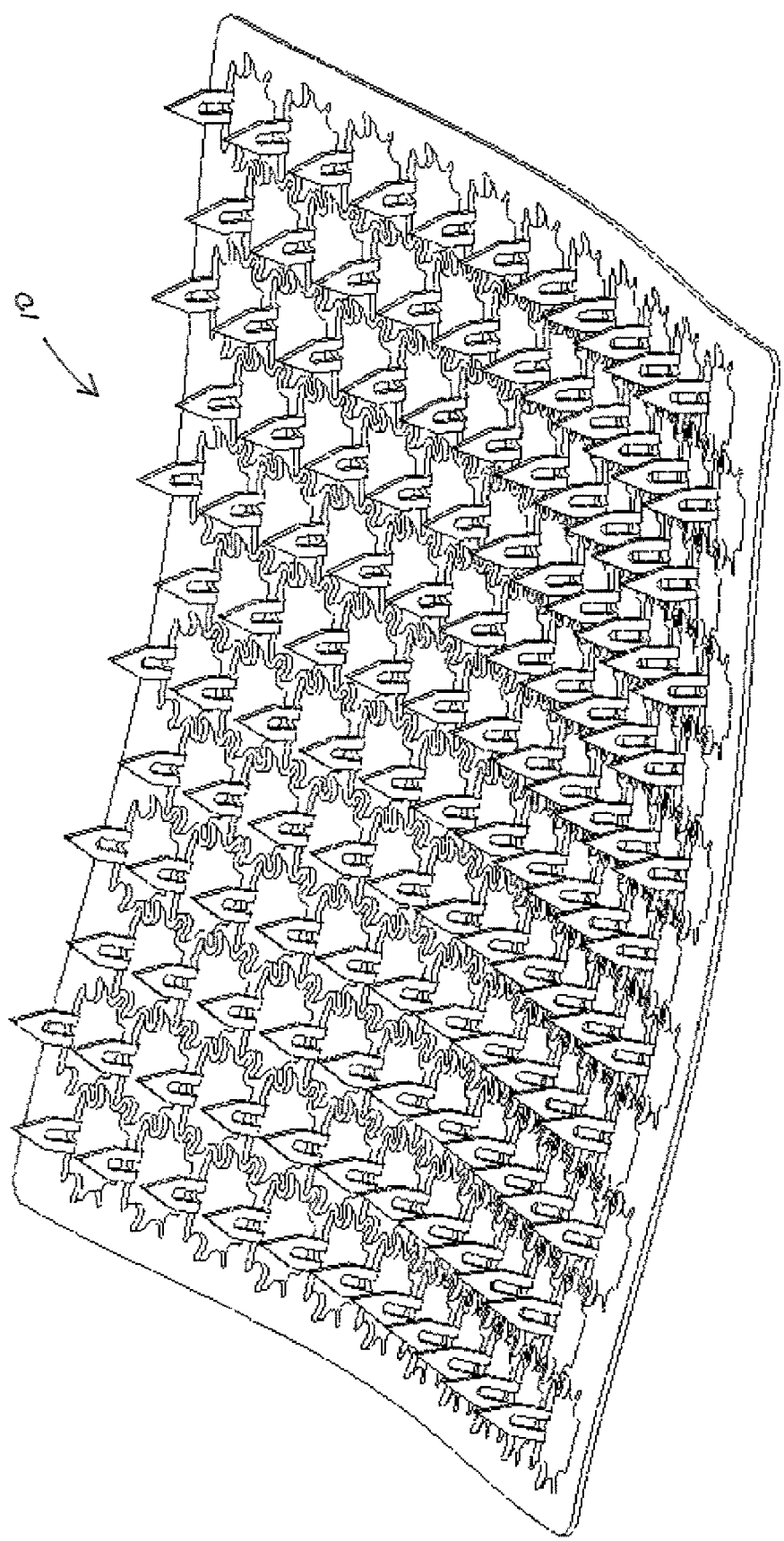
Figure 2C:
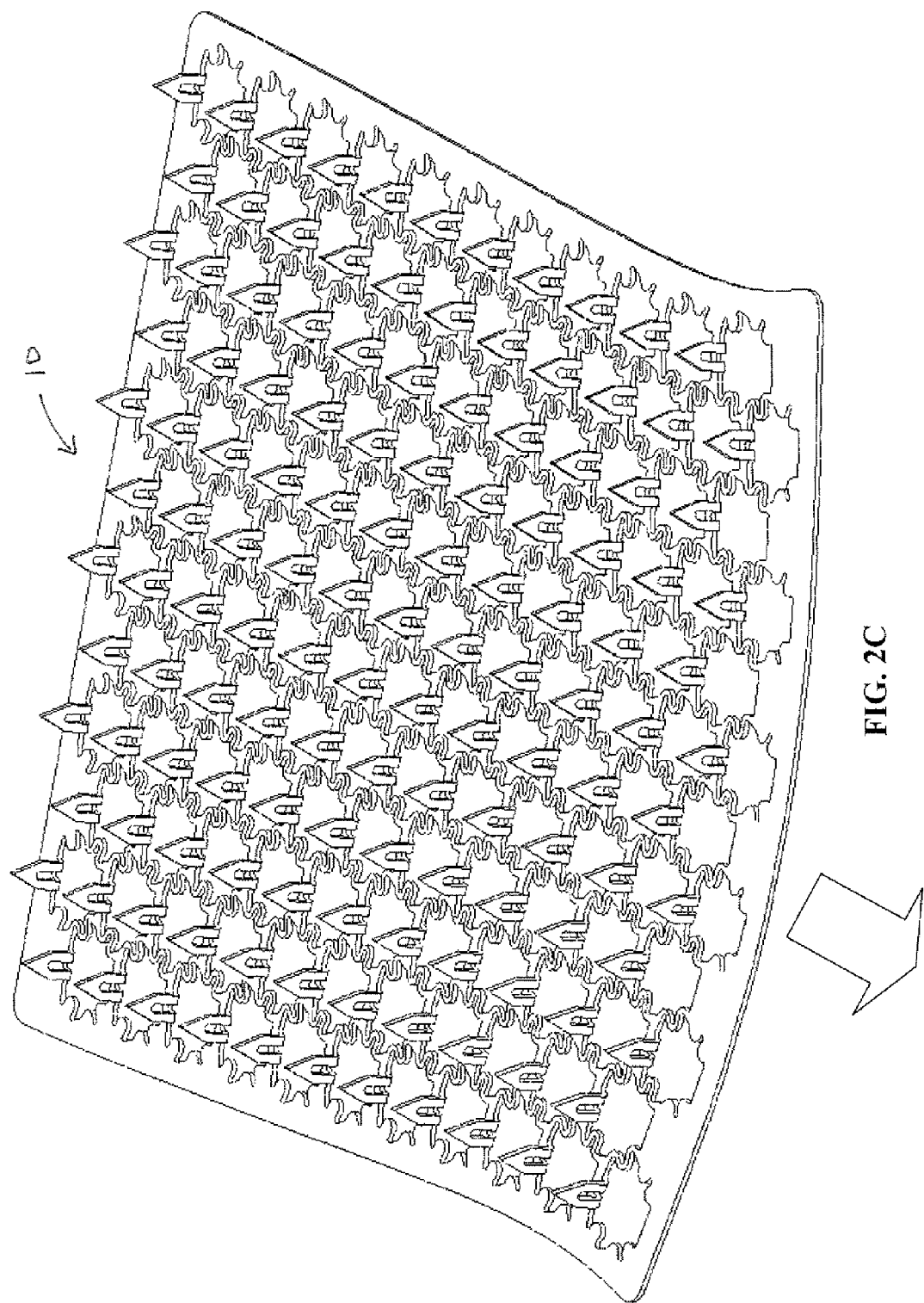
Figure 2D:
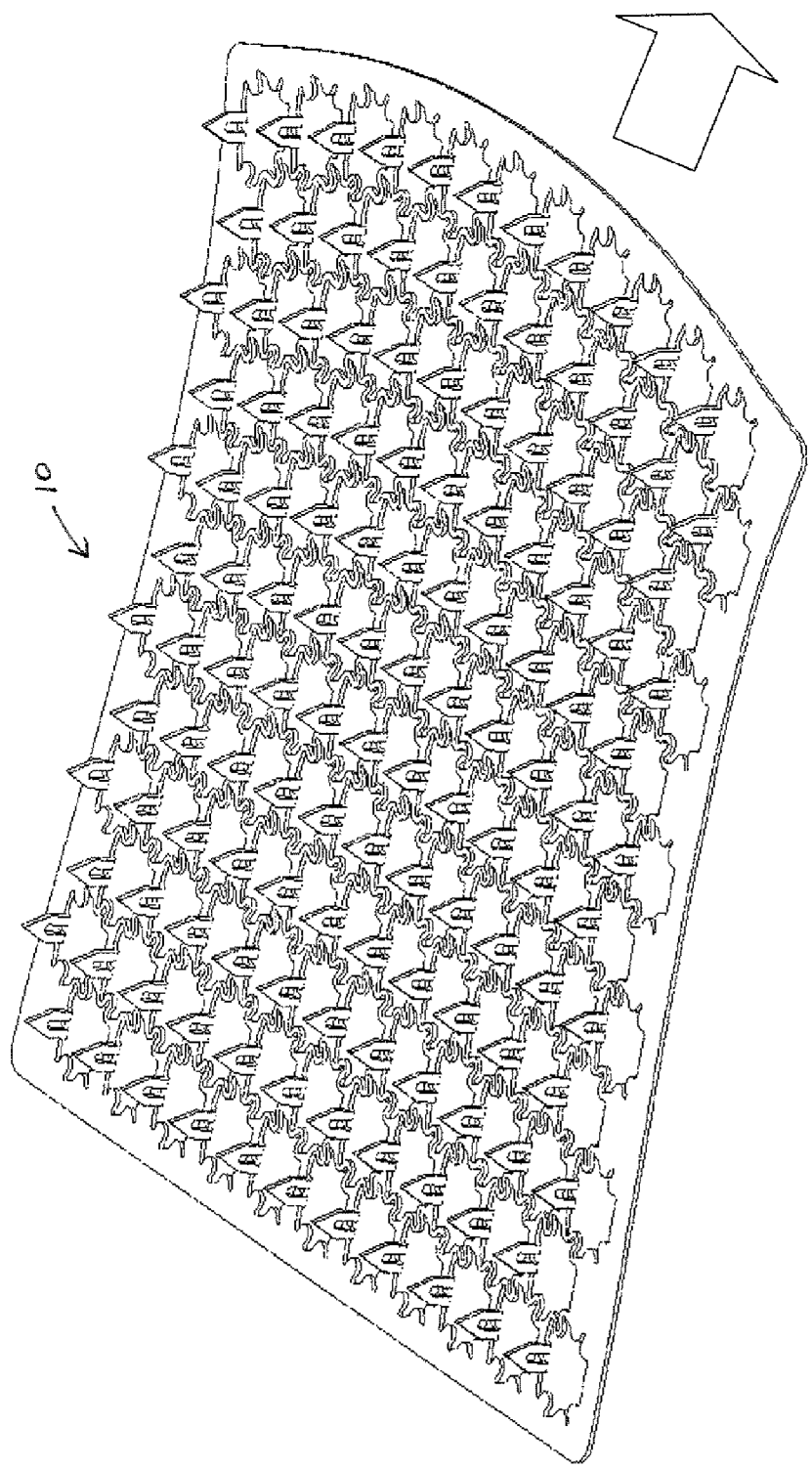

FIG. 2A-D illustrate the conformability and stretchability of the microneedle array 10. FIG. 2A shows the array as it would conform to microneedles inserted into a concave surface (not shown), and FIG. 2B shows the array as it would conform to microneedles inserted into a convex surface (not shown). FIG. 2C-D show the microneedle array as it would elastically deform if stretched in two different directions in the plane of the substrate.

The apertures in the substrate may be in essentially any shape, which is dictated in part by the shape of the substrate elements and spring elements. In various embodiments, the apertures may be approximately square, circular, hexagonal, semi-circular, oval, diamond, triangular, or a combination thereof. In a preferred embodiment, the apertures occupy a substantial area of the substrate, in order to maximize the contact of the drug reservoir with skin and to facilitate adhesion of the microneedle patch device to the skin. As used herein, the term "substantial area of the substrate" means that in a plan view of the substrate of the microneedle device, the apertures compose more than about 40% (e.g., between 50% and 95%, between 60% and 85%) of the total area of the substrate from which the microneedles extend.

The Microneedles

Generally, the microneedle can be in any elongated shape suitable for providing the skin piercing and fluid conduit functions, with minimal pain to the patient. In various embodiments, the microneedle is substantially cylindrical, wedge-shaped, cone-shaped, or triangular (e.g., blade-like). The cross-sectional shape (cut along a plane approximately parallel to the plane in which the substrate substantially lies or approximately perpendicular to the longitudinal axis of the microneedle) of the microneedle, or at least the portion of microneedle that is penetrable into the skin, may take a variety of forms, including rectangular, square, oval, circular, diamond, triangular, elliptical, polygonal, U-shaped, or star-shaped.

In one embodiment, the base portion of the at least one of the microneedles has a substantially rectangular cross-sectional shape in a plane parallel to the substrate. Preferably, this base portion is untapered and the tip end portion which extends from the base portion is tapered, the combination of which is believed to provide a good combination of strength, manufacturing ease, and fluid transport performance.

The tip portion of the microneedle is designed to pierce a biological barrier, e.g., to pierce the stratum corneum of the skin of a patient, to form a conduit through which a fluid can be transported into or out of the patient's tissue. To provide minimal pain to the patient, the tip portion of the microneedle should be sufficiently small and sharp to enable piercing and penetration of the skin with minimal pain. In a preferred embodiment, the tip end portion of the microneedle is tapered from the body portion toward the tip end portion, defining a point or apex at the end of the microneedle. In various embodiments, the tapered tip portion may be in the form of an oblique angle at the tip, or a pyramidal or triangular shape.

In one embodiment, at least one of the microneedles has at least one channel extending substantially from the base portion through at least a part of the body portion, the channel being open along at least part of the body portion and in fluid communication with at least one of the apertures in the substrate. The channel desirably extends from the substrate through the base portion and into the tip portion, to facilitate delivery of the drug well beneath the skin surface or to facilitate collection of the biological sample from beneath the skin surface In one specific variation of this embodiment, the channel is open to two opposing surfaces of the microneedle. In one embodiment, a proximal end of the at least one channel extends to or into the at least one of the interior side surfaces of the substrate. In a preferred embodiment, the channel extends from the substrate through the body portion and into the tip end portion. In an alternative embodiment, the channel may terminate in the body portion of the microneedle and not extend into the tapered tip portion.

In one embodiment, each microneedle in an array has a rectangular cross-sectional shape, an untapered base portion, a tapered tip end portion, and a channel which is open to two opposing surfaces of the microneedle and extends from an aperture in the substrate, through the body portion, and into the tapered tip portion. See FIG. 1. Drug delivery rates and biological sample collection rates can be maintained relatively constant because the created pores are kept open by the microneedles inserted into the patient's stratum corneum, and pain from insertion of the microneedles can be minimized since the tip portion of the microneedles in such an embodiment can be made to have a smaller cross-section and sharper tip than drug-coated solid microneedles or hollow microneedles with a central bore. In addition, mass transport using the microneedles can be increased relative to similarly dimensioned hollow tipped or solid microneedles.

In another embodiment, the microneedles may be solid microneedles. In one embodiment, the microneedle may have at least one channel extending from the base portion through the body portion to the tip end portion, the channel having an opening at the base portion and an opening at the tip end portion. For example, in one embodiment, the microneedle may have a central hollow bore.

The dimensions of the microneedles may vary depending on a variety of factors such as the type of drug to be delivered, the dosage of the drug to be delivered, the type of biological sample to be collected, the skin site where the microneedles are inserted, the amount of biological sample to be collected, and the desired penetration depth. Generally, the microneedles are constructed to provide skin-piercing and fluid delivery and/or collection functions and thus will be designed to be sufficiently robust to withstand insertion into and withdrawal from the skin. Each microneedle has a length of about 1 micrometer (μm) to about 5000 micrometers (μm). More preferably, each microneedle has a length of about 1 μm to about 500 μm. Still more preferably, each microneedle has a length of about 100 μm to about 500 μm. The penetration length of the microneedles into the biological barrier is about 50 μm to about 200 μm. In addition, each of the microneedles has a maximum thickness dimension of 500 μm. The thickness of the microneedle may vary along its length. For instance, the base portion may be wider (thicker) than the body portion, or the body portion may have a slight taper approaching the tip portion.

In one embodiment, the microneedle includes one or more channels. The one or more channels in each microneedle provide a path for a drug formulation to flow from the substrate through/into the biological barrier or for a biological fluid to flow from the biological tissue through/into the substrate at the site of piercing. The channel preferably extends from the substrate toward the tip through a substantial portion of a length dimension of the microneedles. In some embodiments, the channel may not extend all the way to the tip of the microneedle if it is not a central bore. The channel may comprise an opening through two surfaces of the microneedle. In alternate embodiments, the channel may comprise any shape suitable to deliver fluid proximal to the microneedle tip. For example, the channel may comprise a groove on one surface of the microneedle that is only open to the outside environment on one side of the microneedle. In addition, the channel may be dimensioned to provide a capillary force or effect upon the fluid to be delivered such that the capillary effect draws or wicks fluid into the base portion of the microneedle from the substrate, through the body portion of the microneedle, and toward the tip portion of the microneedle. In other embodiments, the channel may be dimensioned to provide a capillary force or effect upon the fluid to be collected such that the capillary effect draws or wicks fluid on or into the microneedle from the biological barrier, through the body portion of the microneedle, and toward the substrate. In other embodiments, each microneedle may have more than one channel, for example, two narrower channels in parallel.

The width of the channel may be constant along its length or may vary. The length of the channel will vary depending on a variety of factors. In a preferred embodiment, the length of the channel may be about 50 to 99% of the length of the microneedle, and preferably is about 70 to 99% of the length of the microneedle. Nevertheless, it is possible that in certain embodiments the length of the channel will be between 1 to 50% of the length of the microneedle. As such, the length of the tip portion beyond the channel may vary, but usually is about 1 to 50% of the length of the microneedle, and more usually is about 1 to 30% of the length of the microneedle. The width of the channel, the length of the channel, and the length of the microneedle may be varied to increase or decrease the flow rate of the drug or the flow rate of the biological fluid.

In one embodiment, the body portion of the microneedle is rectangular with a centrally located channel extending through the opposed longer sides of the body portion. In one particular embodiment, the rectangular body portion has a long side cross-sectional dimension between 1 μm and 500 μm and a short side cross-sectional dimension between 1 μm and 200 μm.

In a preferred embodiment, the microneedle has an untapered, rectangular-shaped base portion having a longer side width of between 50 μm and 500 μm and a shorter side width of between 20 μm and 200 μm. The channel is centrally located in the microneedle and extends from an aperture in the substrate, through the base portion, and into a tapered tip portion, and is open to both of the longer sides of the base portion. In one embodiment, the width of the channel is substantially constant along its length in the base portion. In one case, the width of the channel is between about 40 μm and about 400 μm, e.g., between 100 and 250 μm.

Materials of Construction and Other Details

In preferred embodiments, the substrate, the microneedles, or both, are formed of, or coated with, a biocompatible material. The microneedles may be formed from the substrate material, or alternatively, the microneedles can include a material different from the substrate material. Representative examples of suitable materials of construction include metals and alloys such as stainless steels, palladium, titanium, and aluminum; and polymers such as polyetherimide, polycarbonate, polyetheretherketone, polyimide, polymethylpentene, polyvinylidene fluoride, polyphenylsulfone, liquid crystalline polymer, polyethylene terephthalate (PET), polyethylene terephthalate-glycol modified (PETG), polyimide, and polycarbonate. In a preferred embodiment, the microneedles and substrate consist of a metal or alloy. In another embodiment, the microneedles comprise a biocompatible thermoplastic polymer. In a preferred embodiment, the substrate and the microneedles are formed of the same material.

The microneedle material of construction preferably is selected such that the microneedle is strong enough at its designed dimensions for the microneedle to effectively pierce the stratum corneum or other biological barrier without significant bending or breaking of the microneedle. The microneedle and substrate materials should be non-reactive with any drug formulation being delivered or any analyte sampled.

The substrate, the microneedles, or both, optionally may further include secondary materials of construction embedded therein or coated thereon. For example, microparticles, nanoparticles, fibers, fibrids, or other particulate materials may be included. Examples of such materials include metals, carbon siliceous materials, glasses, and ceramics. These secondary materials may enhance one or more physical or chemical characteristics of the microneedle array. For example, the secondary material may be insulating layer or may improve the flow or transport of the drug formulation through the apertures and channels of the array. Representative examples of suitable insulating materials include PET, PETG, polyimide, polycarbonate, polystyrene, silicon, silicon dioxide, ceramic, glass, and the like. In a preferred embodiment, a channel of the microneedle may include one or more agents to facilitate fluid flow. For example, one or more hydrophilic agents may be present on the interior surfaces defining the channel. Examples of such hydrophilic agents include, but are not limited to, surfactants. Exemplary surfactants include MESA, Triton, Macol, Tetronic, Silwet, Zonyl, and Pluronic.

The surface of the substrate that is in contact with the surface of the biological barrier (e.g., the stratum corneum) may be coated, in whole or in part, with a bonding substance that can secure the microneedle patch to the biological barrier for an extended period of time, e.g., for a duration required to release all of the drug formulation to the biological barrier. Examples of such bonding agents include adhesives and bioactive films, which are activated by pressure, heat, light (UV, visible, or laser), electric, magnetic fields, biochemical and electrochemical reactions, or a combination thereof.

Microneedle Drug Delivery Device

In one embodiment, the microneedle array described herein is included as part of a drug delivery device. The device may include a drug storage element, which is a means for containing a drug formulation for release to and through the microneedle array, for transdermal administration of the formulation via the microneedle array. In another embodiment, the drug formulation may be provided as a coating, applied onto the surfaces of the microneedles and/or the substrate of the microneedle array. Preferably, the drug delivery device is in the form of a transdermal drug delivery patch.

In a preferred embodiment, the drug storage element is positioned adjacent to the substrate. For example, the drug storage element may be attached to a first surface of the substrate, wherein the first surface is opposed to a second surface of the substrate from which the microneedles project. In a preferred embodiment, the drug delivery device is in the form of a patch that can be secured to the skin during transdermal administration of a drug formulation through the microneedle array. In one embodiment, the device includes a backing structure and adhesive surface suitable for securing the device to the skin of a patient with the microneedles in an inserted position in the skin. In a preferred embodiment, the drug formulation comprises an adhesive compound. The inserted microneedles may be secured by non-adhesive means known in the art, such as an elastic band or a strap with hook-and-loop fasteners, which can be wrapped around a patient's limb over the microneedle patch. In a preferred embodiment the microneedles, drug storage element, and/or adhesive surface are protected by a release liner which is removed before administration of the drug delivery patch to the skin.

Figure 4A:
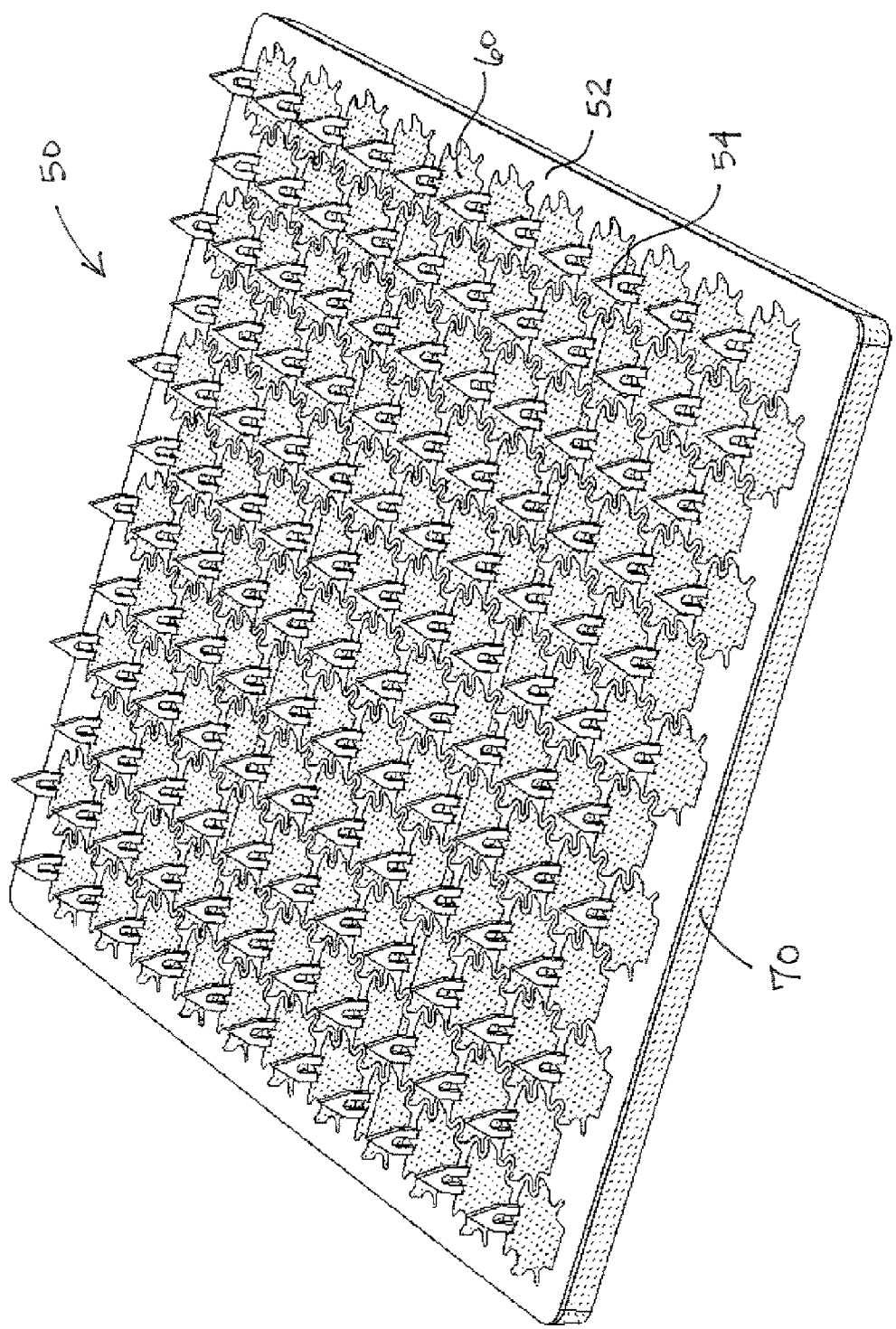
FIG. 4A-B are perspective views of one embodiment of a drug delivery patch which comprise a microneedle array as described herein.
Figure 4B:
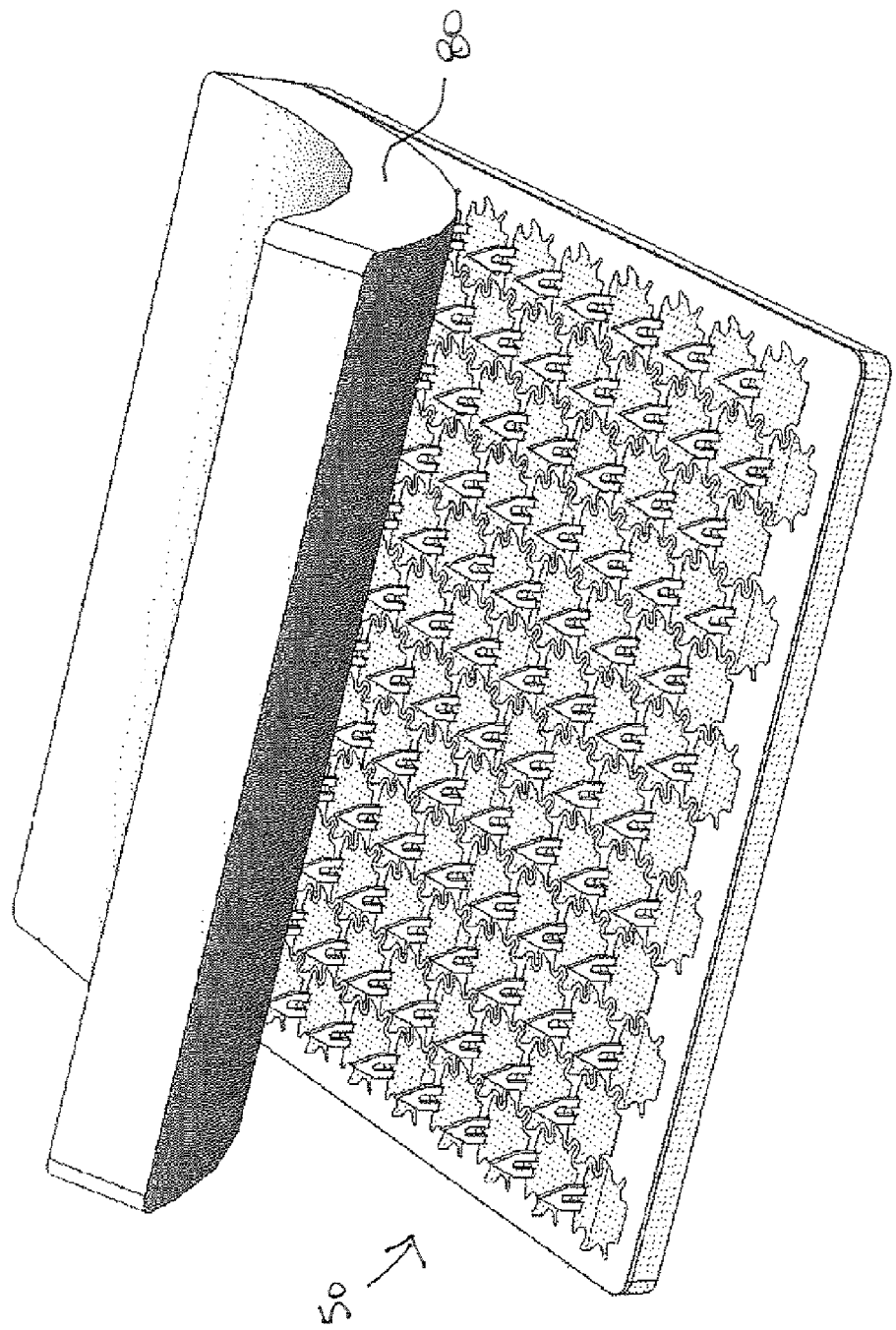

FIG. 4A-B illustrate one embodiment of a transdermal drug delivery patch device 50. As shown in FIG. 4A, the device 50 includes substrate 52, from which an array of microneedles 54 perpendicularly extends. The device 50 also includes a drug storage element 70, which can release drug through apertures 60 in the substrate 52. FIG. 4B shows device 50 with a release liner 80 partially removed to expose the microneedles and drug storage element.

In a preferred embodiment, the drug storage element is flexible and can conform to a contoured, or curved, surface. In one embodiment, the drug storage element can be stretched or compressed in a direction parallel to the plane in which the substrate substantially lies.

In one embodiment, the drug formulation may be contained in a drug storage element and also in the apertures and/or channels of the microneedles. For example, the drug storage element may be applied to the microneedle array and deformed to fill the apertures in the substrate. In another instance, the drug storage element may be applied to the microneedle array with the drug formulation in a liquid form to fill the apertures in the substrate and/or microneedles and then the drug formulation may be dried to a solid or semisolid state.

In one embodiment, the drug storage element completely fills the apertures and contacts the skin upon patch application. In one embodiment, the drug storage element includes an adhesive material and contains a drug formulation, wherein the adhesive material is adapted to adhere to a patient's skin through the apertures, and the drug formulation flows from the drug storage element, through the apertures and the microneedles into the skin tissues beneath the stratum corneum. In variations of this device, the adhesive may adhere to the skin through a portion of the apertures and drug formulation flows through a different portion of the apertures. The apertures may occupy a substantial area of the substrate sufficient to maintain securement of the microneedle array patch on the skin for an extended period.

In a preferred embodiment, the drug storage element has at least one sealed reservoir, which can be selectively punctured or otherwise breached in a controlled manner to release a drug formulation contained therein. In one embodiment, the drug storage element includes a porous material, wherein the drug formulation is stored in pores of the porous material. Representative examples of suitable porous materials include open cell polymeric foams, sheets/mats of woven or non-woven fibers, combinations thereof, and the like. In another example, the drug storage element may be in the form of one or more substantially flat pouches, for example, made of two sheets of flexible thermoplastic polymeric film, sealed along the edges to define a reservoir therebetween.

The "drug formulation" refers to essentially any therapeutic or prophylactic agent known in the art (e.g., an active pharmaceutical ingredient, or API), and typically includes one or more biological acceptable carriers or excipients to facilitate transdermal administration of the drug formulation. In one embodiment, the drug formulation is a fluid drug formulation, wherein the formulation can flow through apertures and/or channels in the microneedle array; it may be a solution, suspension, emulsion, or a combination thereof. In another embodiment, the drug formulation comprises a solid formulation, wherein the transport of drug through apertures and/or channels in the microneedle array, or from the surface of the microneedles, involves diffusional transport mechanisms, with little or no bulk flow. The drug delivery device may include a drug formulation that includes a combination of liquid and solid components, wherein transport of the drug formulation involves both flow and mass diffusion.

The drug delivery device may include a means for causing a drug formulation to be released from the drug storage element, permitting the drug formulation to flow through the apertures in the substrate, through apertures in the stratum corneum formed by the microneedles, and into tissues of the patient, for local, regional, or systemic therapeutic or prophylactic effect. In one embodiment, the release is to and through the apertures in the planar substrate and thus to the base end of the microneedle or channel in the microneedle. In another embodiment, the release is to and through a central bore in the microneedles. A wide variety of release mechanisms for releasing the drug formulation from the drug storage element can be envisioned by those skilled in the art. These release mechanisms may utilize a mechanical force, heat, a chemical reaction, an electric field, a magnetic field, a pressure field, ultrasonic energy, vacuum, pressure, or a combination thereof. In one embodiment, the release mechanism includes a means for applying a compressive force to a porous material to expel the drug formulation from the pores in the porous material. The means for applying a compressive force can be in the form of a spring-biased piston or button that can be manually depressed to apply a direct or leveraged force onto the back of the drug storage element. The same force optionally may cause the microneedles to be inserted into the skin of a patient and/or cause a pressure-sensitive adhesive surface on the device (e.g., inside the apertures and on the periphery of a backing material) to become adhered to the surface of the skin. In another embodiment, the drug delivery device includes at least one puncturing barb extending from the surface of the planar substrate (opposite the microneedle), wherein the puncturing barb can be used to puncture the sealed reservoir, e.g., upon application of a compressive force to the reservoir. This barb could be one or more microneedles bent in the opposite direction from the microneedles intended for skin insertion.

The flow of the drug formulation through the channels or on the microneedles into the biological barrier may be passive, e.g., the result of capillary and gravitational forces. Drug transport may also involve molecular diffusion. Alternatively, the flow may be actively assisted. In one embodiment, the drug delivery device may include means for actively driving the drug formulation through the microneedle channels and/ or on the microneedles and into the skin. For example, the flow of the drug formulation through the channels into the biological barrier may be aided by application of heat (e.g., generated by a series of microfabricated resistors), an electric field, a magnetic field, a pressure field, a concentration gradient, or any other physical force or energy. The application of an electric field can comprise electrophoresis, iontophoresis, electroosmosis, electroporation, or the like. The application of a magnetic field can comprise magnetophoresis or the like. The application of a pressure field can comprise pumping, applying ultrasonic energy, applying vacuum, pressure, or the like.

The optional release liner of the transdermal drug delivery patch is applied to the microneedle to protect the microneedles and/or the drug storage element during manufacture, storage, and/or handling of the patch device. The release liner is removed prior to the application of the microneedle patch to the skin to expose the microneedles and drug storage element. The release liner may be designed to be removed manually or by an applicator device. The release liner is typically thicker that the length of the microneedles. The release liner may be flexible. In one embodiment, the release liner is applied to the microneedle array onto the microneedle side, and then a drug storage element applied to the opposing side of the microneedle array as needed, e.g., immediately before the microneedle array is applied to the skin. The microneedle array and release liner may be rolled up, e.g., for manufacturing, storage, or packaging, without the drug storage element.

Microneedle Device for Fluid Withdrawal

In one embodiment, the microneedle array described herein is included as part of a device for withdrawal of a biological fluid from a patient, such as a diagnostic sensing device. The device includes a collection reservoir for containing a withdrawn sample of a biological fluid from holes in a patient's tissue formed by the microneedle array. Preferably, the fluid withdrawal device is in the form of a transdermal patch. The term "biological sample" or "biological fluid" refers to blood, interstitial fluid, or another biological fluid, or component thereof, which may be withdrawn from a biological tissue of a patient in an amount useful in diagnostic analyses. For example, the biological sample may comprise a blood sample for monitoring glucose, potassium, cholesterol, or other analyte levels indicative of or relating to a medical condition of the patient. As used herein, the term "patient" refers to animals, particularly mammals, and especially humans.

In one embodiment, the collection reservoir is located adjacent to the substrate. The collection reservoir preferably is flexible and able to conform to a contoured surface, along with the microneedle array. The reservoir may be attached to a first surface of the substrate, wherein the first surface is opposed to a second surface of the substrate from which the microneedles project. The biological sample collection device may be in the form of a patch that can be secured to the skin during transdermal withdrawal/collection of a biological fluid sample over an extend period. In one embodiment, the device, or patch, includes a backing structure and an adhesive surface suitable for securing the device to the skin of a patient with the microneedles in an inserted position in the skin. The adhesive surface and/or microneedles of the patch may be protected by a release liner, which is removable before application of the microneedle array patch to the skin.

In one embodiment, the collection device includes an adhesive material adapted to adhere to a patient's skin through the apertures. In variations of this device, the adhesive may adhere to the skin through a portion of the apertures and withdrawn biological fluid flows through a different portion of the apertures. The apertures may occupy a substantial area of the substrate sufficient to maintain securement of the microneedle array patch on the skin for an extended period.

In one embodiment, the biological sample collection device may include one or more sensors in communication with the collection reservoir, one or more of the microneedles, one or more of the apertures, or combinations thereof. The sensor may be a biosensor known in the art, such as an analyte sensor. The sensor may be used to continuously or intermittently monitor an analyte concentration during any period of time during which the microneedle array patch is worn. In one embodiment, the sensor may transmit collected data to an external device for further analysis and/or display to a patient or healthcare provider.

The flow of the biological sample through the holes in the biological tissue barrier (e.g., stratum corneum) made by the microneedles (whether through a channel or bore therein or along the outer surface of the microneedle) may be passive, e.g., the result of capillary and gravitational forces, or may be actively assisted. In one embodiment, the biological sample collection device may include a means for actively driving transport of the biological fluid. The transport assist means may utilize local heat application (e.g., generated by a series of microfabricated resistors), an electric field, a magnetic field, a pressure field, a concentration gradient, or any other physical force or energy. The application of an electric field can comprise electrophoresis, iontophoresis, electroosmosis, electroporation, or the like. The application of a magnetic field can comprise magnetophoresis or the like. The application of a pressure field can comprise pumping, applying ultrasonic energy, applying vacuum, pressure, or the like.

Making the Microneedle Arrays

The microneedle arrays described herein can be made by using or adapting a variety of fabrication techniques known in the art, depending upon the particular materials of construction and the particular microneedle/array design selected. In one embodiment, the microneedle array is made using one or more conventional microfabrication techniques. The microneedles may be formed individually or the whole array of microneedles and substrate may be formed in a single process. In a preferred embodiment, the microneedle arrays are formed in mass (i.e., commercial scale) quantities using inexpensive fabrication processes available in the art.

In one embodiment, the microneedle array is made by a method that includes (a) forming a flexible substrate which comprises a plurality of apertures, each of which are defined by (i) a plurality of substrate elements, and (ii) at least one spring element connecting at least two of the substrate elements; and (b) forming a plurality of microneedles, each having a base portion, a tip end portion distal to the base portion, and body portion therebetween, wherein the base portions of the microneedles are integral with the substrate elements. Steps (a) and (b) may be conducted simultaneously. In one embodiment, the method includes forming in a planar substrate material the plurality of apertures, the plurality of substrate elements, and the plurality of spring elements, by removing selected portions of the substrate material. The removal process may include embossing, injection molding, casting, photochemical etching, electrochemical machining, electrical discharge machining, precision stamping, high-speed computer numerically controlled milling, Swiss screw machining, soft lithography, directional chemically assisted ion etching, laser cutting, or a combination thereof.

The forming of the microneedles may include forming the microneedles in-plane with the substrate and then bending the plurality of microneedles out-of-plane with the substrate, for example, to a position substantially perpendicular to the substrate surface. Alternatively, the microneedles may be fabricated originally out-of-plane with the substrate (i.e., with no intermediate in-plane structure). In a preferred embodiment, photochemical etching can be used to fabricate the metal microneedles that are initially out-of-plane with the substrate. These various microneedle fabrication options allow the microneedle arrays to be fabricated from any type of substrate material.

In a preferred embodiment, microneedles may be formed in-plane or out-of-plane with the substrate using a microreplication technique known in the art. Representative examples of suitable microreplication techniques include embossing, injection molding and casting processes. Such microreplication techniques, and in particular embossing techniques, may provide low cost manufacturing and also may advantageously enable the tip of the microneedle to be extremely small (near infinitesimally small cross-sectional area) and sharp. Furthermore, embossing techniques allow precise, consistent fabrication of the microneedles.

In a preferred embodiment, an embossing technique is used. In one process using an embossing technique, a planar substrate material, such as a suitable thermoplastic precursor material, is placed into an embossing apparatus, where such an apparatus includes a mold having features of a microneedle array as described herein. (The mold may have a negative image of the features of the microneedles, substrate elements, and spring elements.) The precursor material is then compressed by the mold under heat and a suitable compression force. In one embodiment, the substrate material has a thickness in the range of about 25 μm to about 650 μm, preferably from about 50 μm to about 625 μm, and more preferably from about 75 μm to about 600 μm. In one embodiment, the substrate material is heated temperature in the range of about 20° C. to 1500° C., preferably from about 100° C. to 1000° C., more preferably from about 200° C. to 500° C. The heat is usually applied to the substrate material for about 0.1 seconds to 1000 seconds, preferably for about 0.1 seconds to 100 seconds, and more preferably about 0.1 seconds to 10 seconds. The compression force may range from about 1 GPa to 50 GPa, preferably from about 10 GPa to 40 GPa, and more preferably from about 20 GPa to 30 GPa. The compression force may be applied for about 0.01 seconds to 100 seconds, preferably for about 0.01 seconds to 10 seconds, and more preferably about 0.01 seconds to 1 second. The heat and compression force may be applied at the same time or different times. After the substrate material is cooled, it is removed from the embossing apparatus, yielding an embossed array of microneedles, which may be in-plane or out-of-plane. If the microneedles of the embossed array are in-plane with the substrate, then the microneedles subsequently are subjected to a bending step to fix them into an out-of-plane orientation relative to the substrate.

The step of bending in-plane microneedles of an intermediate structure into an out-of-plane position to form a microneedle array can be done using a variety of different methods, to effect application of a direct or indirect force that causes plastic and/or elastic deformation of the microneedles, preferably limited to the base portion thereof. In one example, the bending of the microneedles out-of-plane with the substrate may be facilitated by the use of a mold (e.g., a metal mold) having protrusions corresponding to the number and position of the microneedles in the intermediate structure, whereby the mold can be engaged (e.g., compressed) with the intermediate structure, the compressive force between the protrusions and the microneedles causing all of the microneedles to bend (at their base portions) simultaneously out-of-plane. In another example, the microneedle array can be pressed between a thick elastic film (e.g., rubber or polyurethane) and a mold having cavities corresponding to the number and position of the microneedles to bend the microneedles out-of-plane with the substrate simultaneously. The compressive force squeezes the thick elastic film into the cavities on the opposite side of the substrate, and the thick elastic film consequently bends the microneedles out-of-plane with the substrate and into the cavities.

Heat and/or various auxiliary pressures can be used in conjunction with the bending force to facilitate the bending of the microneedles. For example, a heated high-speed liquid or gas can be flowed in a direction substantially perpendicular to the plane of the substrate comprising plastic microneedles. The plastic microneedles are heated by the flowing fluid, undergo a plastic transition, and then are bent out-of plane with the substrate by the force of the high-speed fluid. In other embodiments, the step of bending the in-plane microneedles may include directly or indirectly applying an electric field or a magnetic field to microneedles.

Figure 3:
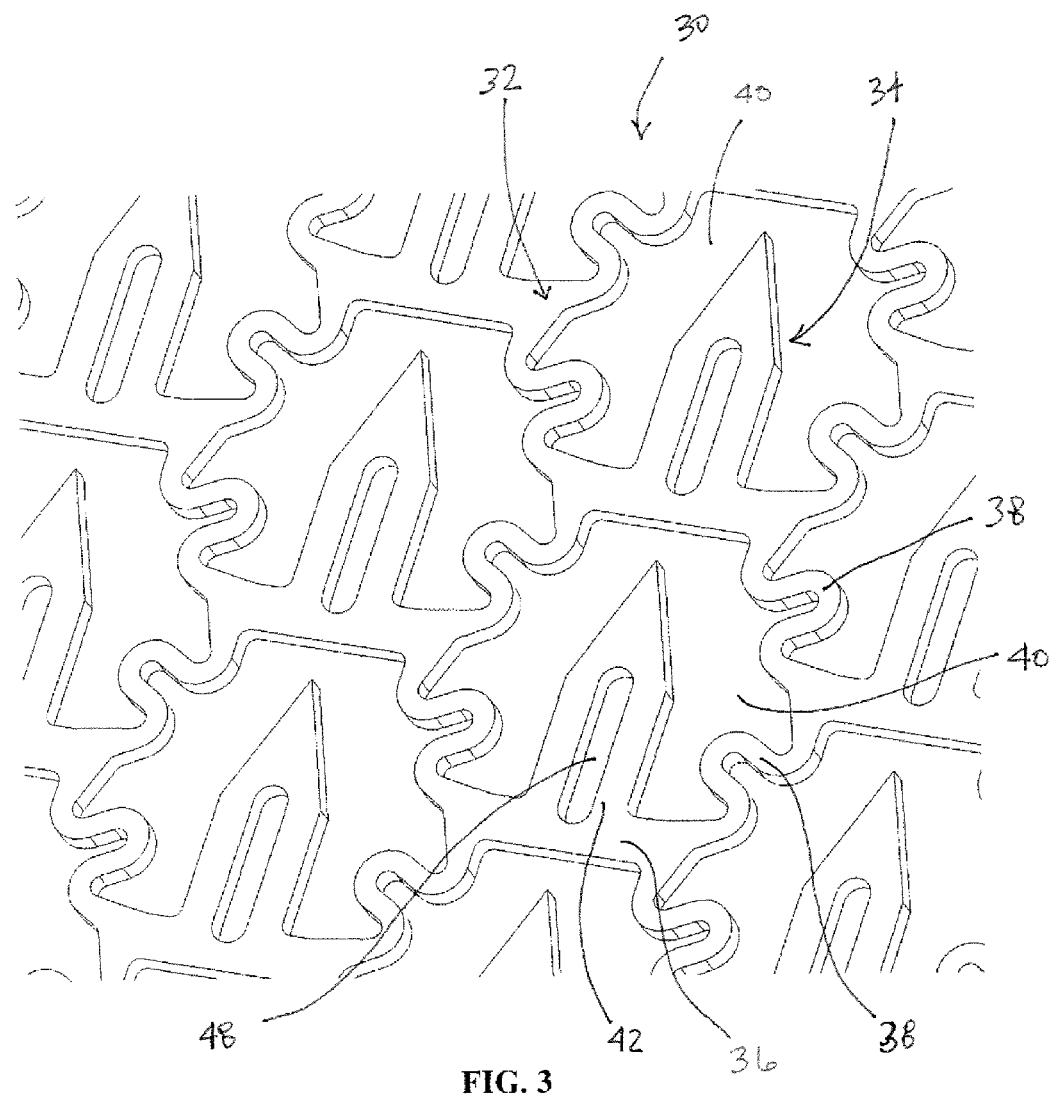
FIG. 3 is a close-up view, perspective view of an intermediate structure made in forming one embodiment of the microneedle array.

FIG. 3 illustrates a close-up view of one embodiment of an intermediate microneedle structure 30. The intermediate structure 30 includes a planar substrate 32 and a plurality of microneedles 34, which lie in the plane of the substrate. The structure 30 includes apertures 40, each of which are defined by one microneedle 34, the long side of two elongated substrate elements 36 (the base portion 42 of the microneedle being integral with one of these substrate elements), the short side of two other elongated substrate elements 36, and four spring elements 38. Each microneedle 34 has an elongated through channel 48, which extends from the substrate element 36 into the tip portion of the microneedle. To complete the microneedle array from this intermediate structure, the microneedles 34 will be bent out-of-plane from the substrate 32. This bending desirably will form a curve segment in the base portion 42 of the microneedle adjacent the substrate element.

The microneedle arrays and drug storage elements or collection reservoir can be made separately and then assembled using techniques known in the art for adapting a conventional microneedle array into a drug delivery or fluid withdrawal device. This assembly and packaging preferably is done in an aseptic or sterile environment.

Use of Devices Which Include the Microneedle Array

Drug delivery devices and biological sample collection devices which include the microneedle arrays described herein may be used to administer a drug formulation to, or withdraw a biological fluid sample from, a patient across a biological barrier. The biological barrier typically is human or other mammalian skin, although other tissue surfaces may be envisioned.

The transdermal administration of a drug to a patient in need thereof may include the steps of (a) inserting into the skin of the patient the microneedles of a drug delivery device that has a drug storage element containing a drug formulation, and then (b) causing the drug formulation to be transported from the drug storage element, and through holes (made by the inserted microneedles) in the stratum corneum of the patient's skin. In one embodiment of a drug delivery device, a drug formulation is released from a drug storage element, and flows to the microneedle array, where it passes through the apertures in the substrate of the array and then enters the channels (or bores, or grooves) in the microneedles at the base of the microneedles. The drug formulation is transported through the channel (or bore or groove), traversing the stratum corneum and then entering the epidermis, dermis, and/or subcutaneous skin tissues. The drug formulation may, in addition or in the alternative, travel along on the outside of the inserted microneedles, to traverse the stratum corneum. After administration of the drug formulation is complete, the microneedles are removed from the skin.

The transport of the drug formulation from the device and through the biological barrier can be passively or actively assisted. In various embodiments, the drug formulation is transported under the influence or assistance of capillary forces, gravitational forces, overpressure, vacuum, an electric field, a magnetic field, iontophoresis, a molecular concentration gradient, or a combination thereof. One skilled in the art can utilize or readily adapt any of these means using technology known in the art.

The transdermal withdrawal of a biological fluid sample from a patient may include the steps of (a) inserting into the skin of the patient the microneedles of a biological sample collection device that has a reservoir, and then (b) causing the biological fluid to be transported from the stratum corneum of the skin, into and through at least one channel of at least one of the microneedle, and to the reservoir. In one embodiment of a biological fluid sampling device, blood or interstitial fluid flows from the epidermis, dermis, and/or subcutaneous skin tissues to the inserted microneedles. The fluid enters the channels (or bores, or grooves) in the microneedles, and/or travels along on the outside of the inserted microneedles, to traverse the stratum corneum, where it passes through the apertures in the substrate of the array and then into a collection reservoir. After withdrawal of an appropriate sample size, or upon completion of an extended diagnosis or sensing period, the microneedles are removed from the skin.

The transport of the biological fluid can be passively or actively assisted. In various embodiments, the biological fluid is transported under the influence or assistance of capillary forces, gravitational forces, overpressure, vacuum, an electric field, a magnetic field, iontophoresis, a molecular concentration gradient, or a combination thereof. One skilled in the art can utilize or readily adapt any of these means using technology known in the art.

The microneedles of the disclosed devices can be inserted into the skin by a variety of means, including direct manual application or with the aid of an applicator device to insure uniform and proper microneedle penetration, consistently within a single array and across different arrays. The applicator device may be completely mechanical or it may be electromechanical. The applicator device may include pressure sensors in communication with an electronically controlled release mechanism, to insure that a device is applied to the skin with the desired force each time. Optionally, the applicator device may include hardware, software, and power source components to provide heat, electrical field, magnetic field, pressure, or other drug delivery assistance means known in the art. In addition, the applicator device may also automatically remove the release liner from the microneedle patch before or during the application of the microneedle patch to the skin. The applicator device may include one or more rollers for use in applying an even pressure to the patches described above to ensure that it is completely secured to the skin. The roller may, for example, further secure a pressure sensitive adhesive surface around the periphery of the patch.

Publications cited herein are incorporated by reference. The foregoing description of various embodiments of the present invention is presented for purposes of illustration and description. The description is not intended to be exhaustive or to limit the invention to the precise form disclosed. The embodiments were chosen and described in order to best illustrate the principles of the invention and its practical application to thereby enable one of ordinary skill in the art to best utilize the invention and various embodiments with various modifications as are suited to the particular use contemplated. Modifications and variations of the methods and devices described herein will be obvious to those skilled in the art from the foregoing detailed description. Such modifications and variations are intended to come within the scope of the appended claims.

I claim:

1. A microneedle array for use on a contoured or flexible tissue surface comprising:
   a plurality of microneedles, each having a base portion, a tip end portion distal to the base portion, and a body portion between the base portion and the tip end portion; and
   an elastically stretchable substrate which comprises a plurality of apertures, each of which are defined by both: (i) a plurality of substrate elements which are integral with the base portions of the microneedles, and (ii) at least one spring element integral with and connecting at least two of the substrate elements,
   wherein said at least one spring element is configured to allow the substrate to stretch when attached to and worn on the tissue surface.

2. The microneedle array of claim 1, wherein the spring element comprises a curved element.

3. The microneedle array of claim 2, wherein the curved element is C-shaped, U-shaped, or S-shaped.

4. The microneedle array of claim 1, wherein at least one of the apertures is defined by two substrate elements.

5. The microneedle array of claim 1, wherein each substrate element is connected to three or four spring elements.

6. The microneedle array of claim 1, wherein at least one of the plurality of microneedles has a channel extending substantially from the base portion through at least a part of the body portion, the channel being open along at least part of the body portion and in fluid communication with at least one of the apertures in the substrate.

7. The microneedle array of claim 6, wherein the base portion of the at least one of the microneedles is untapered and has a substantially rectangular cross-sectional shape in a plane parallel to the substrate.

8. The microneedle array of claim 7, wherein the at least one channel is open to two opposing surfaces of the microneedle.

9. The microneedle array of claim 6, wherein the tip end portion of the at least one of the microneedles is tapered.

10. The microneedle array of claim 9, wherein the at least one channel extends into the tapered tip end portion.

11. The microneedle array of claim 1, wherein the elastically stretchable substrate and the microneedles are formed of a biocompatible metal or polymer.

12. The microneedle array of claim 11, wherein the elastically stretchable substrate and the microneedles are formed of a biocompatible metal and the biocompatible metal comprises a stainless steel.

13. The microneedle array of claim 1, wherein the length of the plurality of microneedles is between 100 μm and 500 μm.

14. A skin patch for therapeutic or diagnostic applications comprising:
   a microneedle array which comprises
      a plurality of microneedles, each having (i) a base portion, a tip end portion distal to the base portion, and a body portion between the base portion and the tip end portion, and (ii) a channel extending substantially from the base portion through at least a part of the body portion, the channel being open along at least part of the body portion;
      an elastically stretchable substrate which comprises a plurality of apertures, each of the apertures being defined by both: (i) two or more substrate elements which are integral with the base portions of the microneedles, and (ii) at least one spring element integral with and connecting the two or more substrate elements,
      wherein the channels of the microneedles are in fluid communication with at least one of the apertures in the substrate; and
   an adhesive material for securing the microneedle array to a patient's skin with the microneedles inserted into the stratum corneum,
   wherein said at least one spring element is configured to allow the substrate to stretch when attached to and worn on the patient's skin.

15. The skin patch of claim 14, wherein the spring element comprises a curved element.

16. The skin patch of claim 15, wherein the curved element is C-shaped, U-shaped, or S-shaped.

17. The skin patch of claim 14, wherein each substrate element is connected to three or four spring elements.

18. The skin patch of claim 14, wherein the base portion of at least one of the microneedles is untapered and has a substantially rectangular cross-sectional shape in a plane parallel to the substrate.

19. The skin patch of claim 18, wherein the at least one channel is open to two opposing surfaces of the microneedle.

20. The skin patch of claim 14, wherein the tip end portions of the microneedles are tapered.

21. The skin patch of claim 20, wherein the at least one channel extends into the tapered tip end portion.

22. The skin patch of claim 14, wherein the elastically stretchable substrate and the microneedles are formed of a biocompatible metal.

23. The skin patch of claim 14, wherein the elastically stretchable substrate and the microneedles are formed of a biocompatible polymer.

24. The skin patch of claim 14, further comprising a drug storage element for releasing a drug formulation to the patient's skin.

* * * * *